United States Patent [19]

Harkensee et al.

[11] Patent Number: 5,152,740
[45] Date of Patent: Oct. 6, 1992

[54] INFLATABLE HAND SPLINT

[75] Inventors: Patricia M. Harkensee, Mequon; Janet M. Dobbs, Milwaukee, both of Wis.

[73] Assignee: Smith & Nephew Rolyan, Inc., Menomonee Falls, Wis.

[21] Appl. No.: 625,868

[22] Filed: Dec. 11, 1990

[51] Int. Cl.⁵ ................................................ A61F 5/04
[52] U.S. Cl. .......................................... 602/13; 602/5; 128/DIG. 15; 128/DIG. 20
[58] Field of Search ............... 128/DIG. 15, DIG. 20, 128/895, 846, 847; 602/5, 6, 13, 21, 22

[56] References Cited

U.S. PATENT DOCUMENTS

| | | | |
|---|---|---|---|
| 891,533 | 6/1908 | Gibbs | 128/DIG. 20 X |
| 3,547,112 | 12/1970 | Courtney | 128/DIG. 15 X |
| 4,263,905 | 4/1981 | Couch, Jr. | 128/DIG. 20 X |
| 4,628,911 | 12/1986 | Bornstein | 128/DIG. 20 X |
| 4,671,258 | 6/1987 | Barthlome | 128/DIG. 20 X |
| 4,807,606 | 2/1989 | Hasegawa et al. | 128/DIG. 20 X |
| 4,907,574 | 3/1990 | Hollerbach | |

FOREIGN PATENT DOCUMENTS

| | | | |
|---|---|---|---|
| 735700 | 6/1966 | Canada | |
| 817521 | 7/1959 | United Kingdom | 128/DIG. 20 |

Primary Examiner—Robert A. Hafer
Assistant Examiner—Sam Rimell
Attorney, Agent, or Firm—Pravel, Gambrell, Hewitt, Kimball & Krieger

[57] ABSTRACT

The present invention relates to a hand splint which is formed of a bladder adapted to fit in the palm of a patient's hand between the thumb and fingers and two pairs of straps for securing the splint to the hand. The bladder is selectively inflatable and deflatable to fit the need of the patient.

14 Claims, 3 Drawing Sheets

INFLATABLE HAND SPLINT

FIELD OF THE INVENTION

This invention relates to an inflatable hand splint, which is particularly useful for patients with a spastic hand.

BACKGROUND OF THE INVENTION

The subject invention is particularly suitable for splinting a spastic hand. A patient suffering from a neurological defect may experience uncontrollable hand movement. Rigid splints, which typically hold the fingers in an extended position, are difficult to apply when the fingers are in a coiled or semi-coiled position. There is no known device which can be placed under coiled or semi-coiled fingers to gradually move them away from the palm as the condition becomes less severe.

A splint which can be placed between the fingers and palm is important to prevent the patient from digging his or her fingernails into the skin causing lacerations and skin break down which could become infected. Further, a patient with a continuously clenched fist will sweat causing a build up of bacteria with resultant infection.

There is a need for a device that is easily placed in a spastic hand to resist clenching and which can be used to gradually open the fingers while preventing the patient from injuring him or herself.

Applicant is not aware of any prior art directed to inflatable hand splints capable of solving these problems. The closest prior art known are devices for exercising the hand disclosed in U.S. Pat. No. 4,907,574 and Canadian patent 735,700. Both devices are essentially gloves having an inflatable bladder on the palm side of the glove. In Canadian patent 735,700 there is inserted into the palm side of the glove a hand-shaped bladder so that the elongated portions of the bladder reach into the finger spaces of the glove. The bladder is held in place by glue. The paralyzed hand is inserted into the glove such that the palm and fingers overlie the bladder. To extend the fingers, the bladder is inflated with air through a nipple extending through the palm side of the glove.

In U.S. Pat. No. 4,907,574, the glove and bladder are detachable, which offers the economic advantage that each component can be replaced separately as it wears out. One embodiment, designed for exercise of the hand, has an inflatable bladder attached to a glove at the base of the fingers. The hand is inserted into the glove without directly contacting the bladder. The bladder, which inflates to a cylindrical shape, pushes against the base of the fingers as it inflates, causing the fingers to partially unclench. An alternative embodiment employing two bladders, one bladder attached at the wrist and the other bladder attached at the base of the fingers, is useful for fully straightening the fingers and for exercising the wrist.

As is readily apparent, devices such as those disclosed in U.S. Pat. No. 4,907,574 and Canadian patent 735,700, which require a glove, would be unsuitable for application to a spastic hand because of the difficulty of inserting coiled or semi-coiled fingers in a glove. A glove would also limit air circulation and increase the risk of infection.

SUMMARY OF THE INVENTION

The invention solves the problems discussed above by providing an inflatable hand splint which includes a bladder that assumes a substantially cylindrical shape upon inflation. The bladder can be placed in the patient's hand, between the fingers and palm, and then inflated.

In a preferred embodiment, the bladder is secured by a VELCRO ® fastening system having a pair of loop gender straps disposed at one end of the bladder and a pair of grappling gender straps disposed at the opposite end such that two continuous bands of fabric, extending from one end of the bladder to the other, are formed by a VELCRO ® lock. The use of a bladder constructed of polyurethane-laminated nylon twill gives the bladder a long useful life as measured by cycles of inflation and deflation. The bladder can be selectively inflated or deflated depending on the needs of the patient.

DETAILED DESCRIPTION OF A PREFERRED EMBODIMENT

Figures 1, 2:
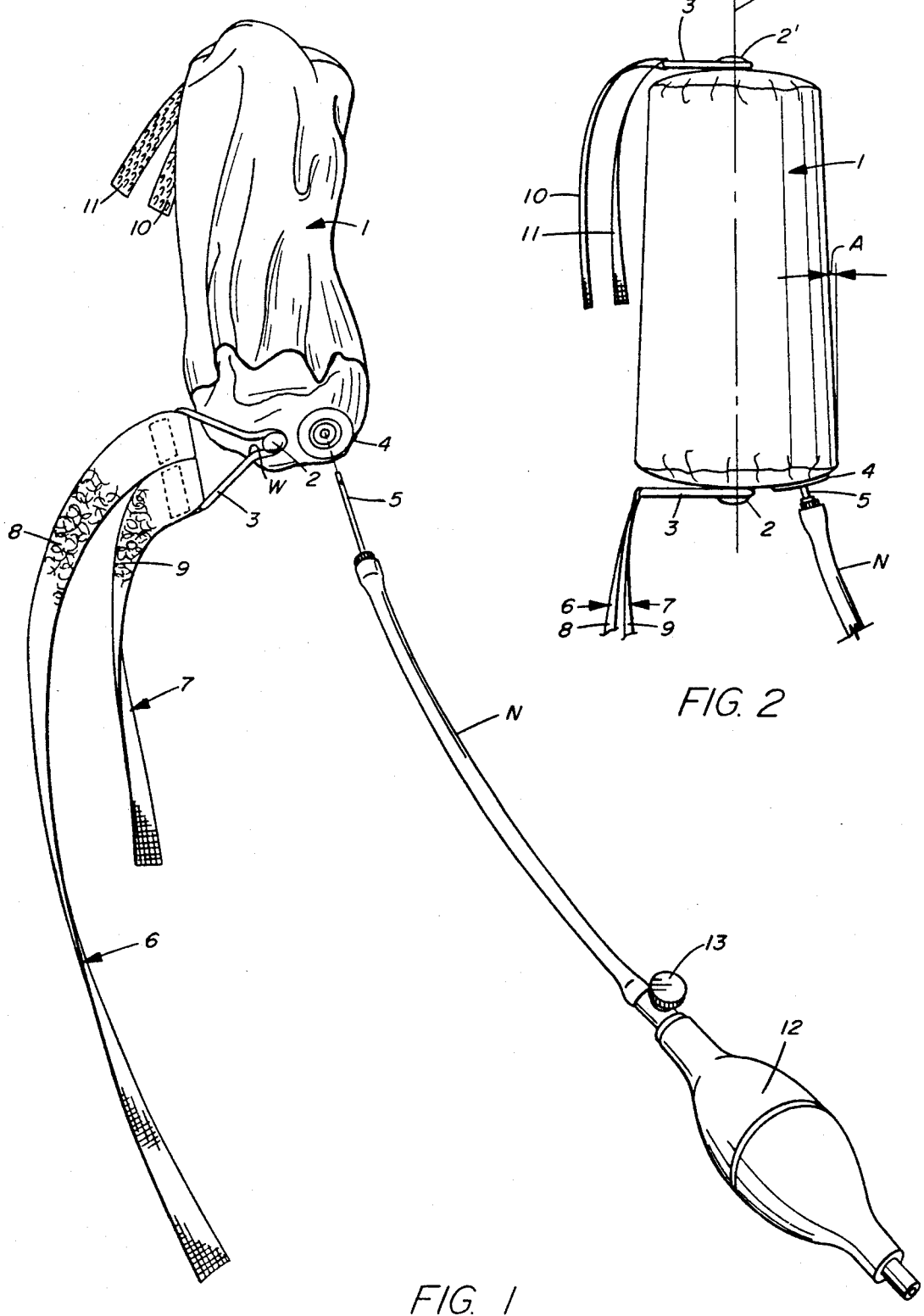
FIG. 1 is a perspective view of the elements of the invention prior to inflation of the bladder.
FIG. 2 is a side view of the bladder of FIG. 1 after inflation.

As shown in FIGS. 1 and 2, the hand splint of the invention is made up of an inflatable bladder 1 which is generally cylindrical in shape upon inflation. As shown best in FIG. 2, the tubular surface of the bladder is, preferably, tapered approximately five degrees, as shown by angle A, relative to the longitudinal axis B of the bladder 1 to achieve a more natural fit to the contours of the hand.

Buttons 2, 2' are formed at the radial centers of the opposing faces of the bladder, as shown in FIG. 2, the faces being formed of an air impermeable, resilient material. The buttons 2, 2' preferably have a cylindrically-shaped inner stem of sufficient height to accommodate clips 3, 3' for securing the bladder 1 to the hand as described below.

An enlarged portion on the end of each stem, which may be an integral portion of a unitary member, prevents the clip from falling off the button 2, 2'. While buttons as described are preferred, other means for securing straps to the bladder could be used, such as, for example, buttons with a hole through them through which a pin may be inserted to secure a positioning means. While the buttons 2, 2' may be formed of any non-porous resilient material, a molded thermoplastic material is preferred.

An inflation port 4 is formed on the larger of the two opposing surfaces of the bladder, adjacent to the centrally located button, for inflating the bladder. The port 4 is capable of forming a gas tight seal against a pressure of at least about 20 pounds and includes a disk with a hole through it, similar to inflation valves used in basketballs, footballs or the like. A flapper of elastomeric material (not shown) is formed on one side of the disk and aligned with a hole, which is capable of forming a gas tight seal to prevent an out rush of air against a gas pressure exerted against the side of the disk to which the flapper is attached. A hollow needle 5, through which air may be pumped, is inserted into the hole to inflate the bladder, thus displacing the flapper and permitting air to be pumped through the valve.

The bladder 1 can be formed of a highly durable, gas impermeable, or, alternatively, a water-permeable, gas-impermeable, material. In one embodiment of the invention, the bladder is constructed of polyurethane-laminated fabric, preferably nylon twill. While the polyurethane laminate provides an airtight barrier, the nylon twill provides a support which is compact when deflated and well adapted to repetitious cycles of inflation and deflation. An extended useful life is thereby afforded by the material over alternatives such as unsupported elastomers. The bladder is formed by rolling a sheet of laminated nylon fabric into an appropriately sized, tapered cylinder and bonding the edges by sonic welding. The ends of the cylinder are then capped with like material and sonic welded to the cylinder to create an air tight bladder.

In an alternative embodiment the bladder 1 can be constructed of an unsupported, water-permeable, gas-impermeable fibrous material such as GORTEX ®, to provide an absorbent bladder. While it is contemplated that continuous use of the invention will typically extend for a day or less, a use may arise which requires continuous use for several days or more. For such use, it is preferable to have a bladder which can draw off sweat wherever the skin contacts the bladder. By constructing the bladder of water-permeable, gas-impermeable material this advantage is realized. However, economic considerations attendant to the cost of producing water-permeable, gas-impermeable materials and the shortened useful life of the bladder as measured by inflation, deflation cycles make use of such materials less preferred than a polyurethane-laminated fabric.

In order to splint a spastic hand, the inflatable splint must be secured to the hand to prevent slippage. Accordingly, a loop and grappling gender fastening system, ie. VELCRO ® fasteners, are provided for securing the splint to the patient's hand. The triangular clips 3, 3' are used to connect the VELCRO ® fasteners to the inflatable bladder 1. One apex of each triangular clip is elongated to provide a loop for engaging the buttons 2, 2'. Accordingly, the widest portion of the loop is of a diameter slightly larger than the stem of the button to which it is engaged and slightly smaller than the diameter of the enlarged portion of the button. Preferably, the loop narrows to a width W less than the diameter of the stem at the segment adjacent to the two flat edges of the triangle forming the apex to lock the clip onto the button. In this preferred design, the clip may be unlocked by the application of force against the side of the triangular clip opposite the loop, forcing the stem through the constriction.

Two straps formed of high-strength, flexible, fibrous material 6, 7, about one inch in width, are connected to each clip 3. The straps are connected by wrapping one end of each strap over the side of the triangular clip opposite the loop and affixing that end to the other portion of the strap, either by stitching or by heat sealing the end to the strap when a meltable material such as nylon is used. As shown in FIG. 1, strap 6, being about eight inches or greater in length, is somewhat longer than strap 7, which is about four inches in length. These straps can be formed of any high-strength, tight weave fabric, in which case a loose-weave fabric providing a suitable loop gender of a VELCRO ® fastening system must be applied to the near surfaces 8, 9, respectively, of the straps 6, 7 as shown in FIG. 1. Preferably, however, the straps are made of a loose-weave fabric suitable for use as the loop gender of a VELCRO ® fastening system which also has high tensile strength. One such fabric is called VELCRO ® laminate.

Figure 3:
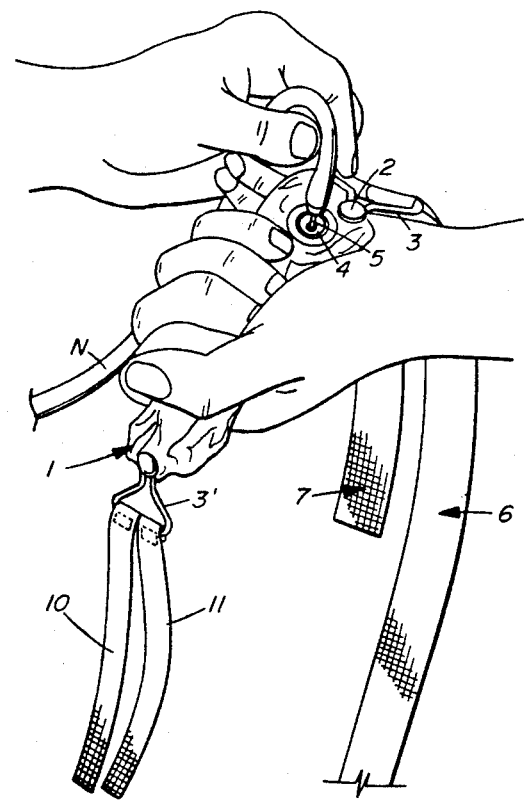
FIG. 3 is a perspective view of the hand splint properly positioned in a patient's hand before the bladder is inflated.

As best shown in FIG. 3, a pair of straps 10, 11, each having a width of about one-half inch and a length of about four inches, are connected to the clip 3'. These straps are connected to the clip 3' by forming the strap into a band around the side of the clip opposite the loop, such that each strap is positioned side-by-side as shown in FIG. 3. These straps are made from any fabric that may be used as the grappling gender of a VELCRO ® fastening system.

The bladder is inflated by pumping air from a bulb 12 such as the type used to inflate a blood pressure cuff. A petcock 13 is connected to the bulb which, in its closed position, permits one-way passage of air from the bulb to the bladder. Opening the petcock bleeds air from the bladder at a controlled rate, thus permitting partial or complete deflation of the bladder. A conduit N is connected at one end to the petcock, and at the other end to a hollow inflation needle 5. The needle is matched to the port 4 to provide a substantially airtight seal during inflation.

In order better to illustrate the use of the invention, relevant descriptive terms relating to the hand are defined. The proximal side of the hand refers to a portion of the hand near the wrist. The radial side is the thumb side of the hand, and ulnar refers to the side of the hand away from the thumb. The latter two terms correspond to the relative positions of the bones of the forearm relative to the hand.

To apply the splint to the hand of a patient, the VELCRO ® fasteners should be clipped to the bladder with the fastening surfaces facing away from the bladder, and with the loop gender straps clipped to the same side as the inflation port. When applied to a spastic hand, the bladder can easily be placed on the palm while initially deflated, as shown in FIG. 3. The bladder is then inflated by inserting the needle 5 into the port 4 and pumping the bulb 12 while the petcock 13 is closed until the bladder assumes a generally cylindrical shape. The bladder is inflated to the desired level as shown in FIG. 4, with the loop gender straps on the ulnar side of the hand, and the thumb laid over the bladder.

Figure 4:
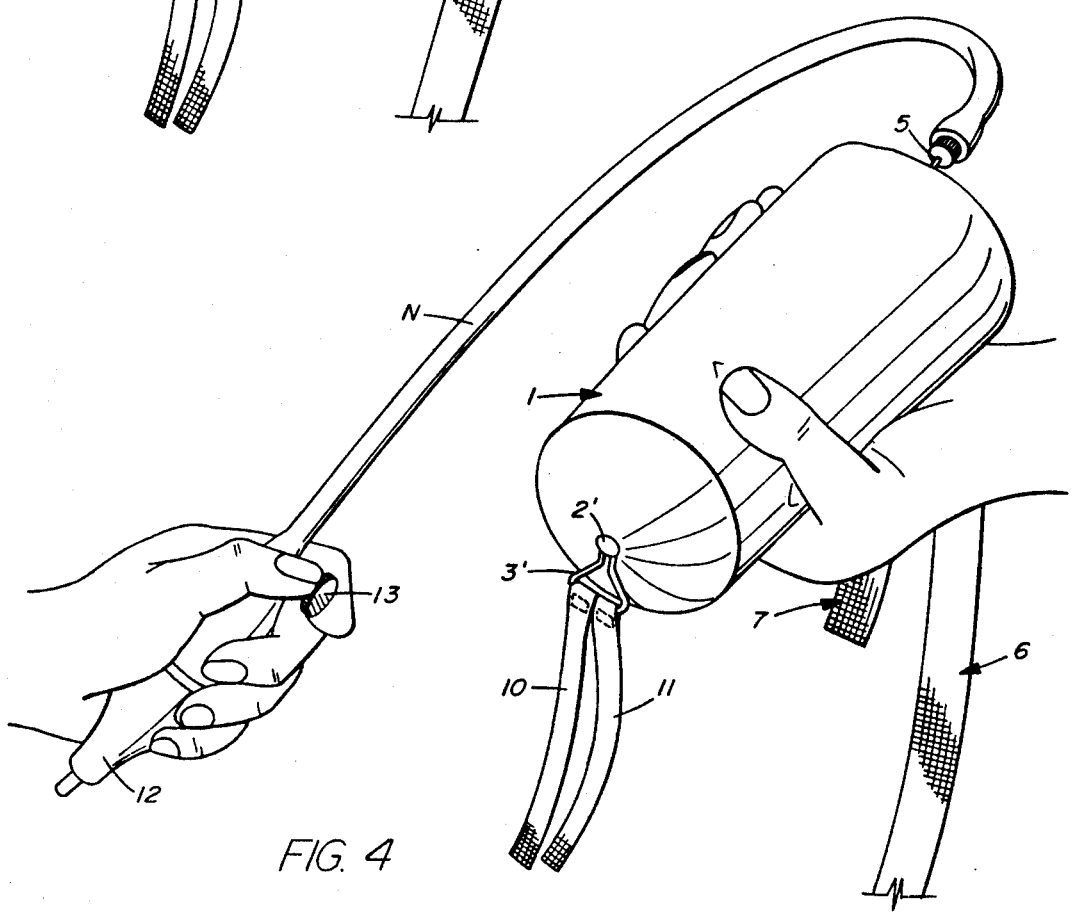
FIGS. 4-7 are a sequence of perspective views showing steps for securing the splint to a patient's hand.
Figure 5:
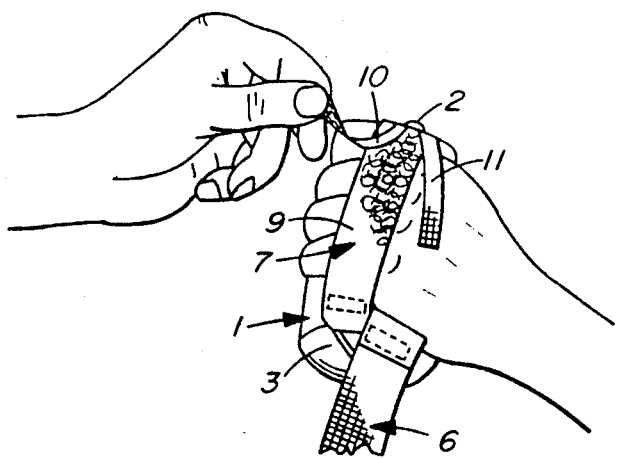
Figure 6:
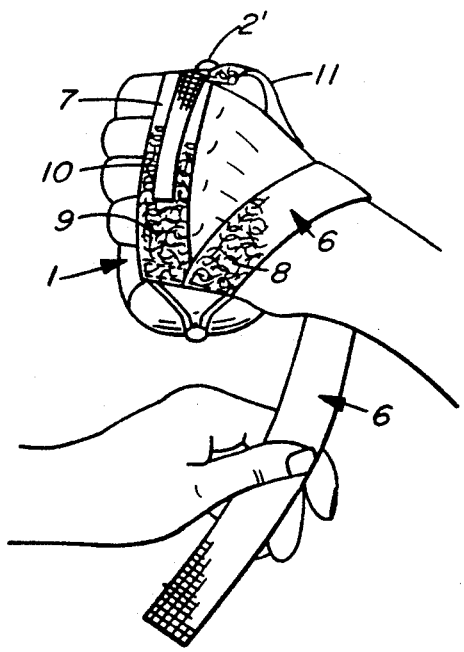
Figure 7:
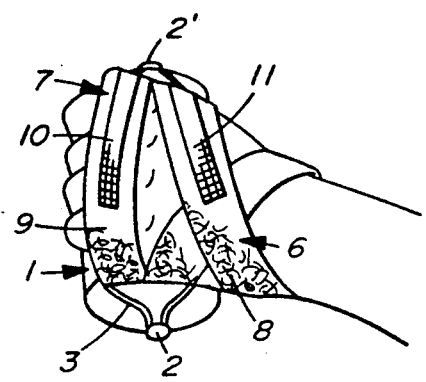

As also shown in FIG. 4, the strap 6 is positioned on the proximal side of the hand relative to the strap 7, which in turn is drawn across the first digits of the fingers as shown in FIG. 5 and fastened in place by the strap 10, forming a VELCRO ® lock. As shown in FIG. 6, the strap 6 is then drawn over the metacarpals, on the side of the knuckles opposite the first digits of the fingers, and wrapped around the wrist on the palm side of the hand, emerging below the thumb. The strap 6 is then fastened in place by the strap 11, to form a VELCRO ® lock, as seen in FIG. 7. The fit between the bladder 1 and the patient's hand may be adjusted by opening the petcock 12 to bleed out air or by further inflation. The conduit and inflation needle may then be detached.

The splint made in accordance with the invention offers the advantages of being able to be applied easily to a spastic hand when the fingers are in a coiled or partially coiled position. The splint is also continuously adjustable for holding the fingers in any of a wide range of coiled and partially coiled positions, as necessary to adjust to the needs of the patient. Moreover, the splint is better adapted to restraining the hand during a spastic episode because of the ease with which it can be positioned and secured.

Although the present invention has been described with reference to its preferred embodiments, those skilled in the art will recognize changes which may be made in form or structure which do not depart from the spirit of the invention already described in the specification and embodied in the claims which follow.

What is claimed is:

1. A hand splint, comprising:
   a. a bladder shaped and dimensioned to be held in the palm of a human hand, constructed of substantially gas impermeable material, which upon inflation assumes a shape adapted to fit in the said palm between the thumb and fingers of the hand the fingers having first digits and knuckles;
   b. securing means for releasably securing the fingers in a semi-coiled position to the bladder at least along the first digits of the fingers and the portion of the hand on the side of the knuckles opposite the first digits;
   c. inflating means for selectively inflating and deflating the bladder for regulating the compression on the hand between the securing means and bladder and for immobilizing and supporting the hand, whereby the fingers can be maintained in an immobilized position.

2. The hand splint of claim 1, wherein the bladder is generally cylindrical in shape with opposite end portions, one end portion slightly smaller than the other to fit in the palm of a human hand.

3. The hand splint of claim 1, wherein the bladder is formed of a gas impermeable material.

4. The hand splint of claim 3, wherein the material is an elastomer.

5. The hand splint of claim 1, wherein the bladder is constructed of gas-impermeable, moisture permeable material.

6. The hand splint of claim 1, wherein the securing means includes pairs of straps connected to opposite ends of the bladder means, means for attaching the straps of each pair to the straps of the other pair.

7. The hand splint of claim 6, wherein the means for fastening the straps includes a loop and grappling gender fastening system.

8. The hand splint of claim 6, wherein the bladder includes a fastening button at each end, a wire clip adapted to be releasably connected to each button, each pair of straps being connected to one of the clips.

9. The hand splints of claim 1, wherein the inflating means includes a one-way valve in the bladder, a pump bulb with a petcock with one-way and two-way flow positions in the bulb, and an inflation needle for connecting the bulb with the bladder through the one-way valve.

10. A hand splint, comprising:
    a. an inflatable body formed of a gas-impermeable material which is generally cylindrical in shape and adapted to fit in the palm of a human hand between the thumb and fingers;
    b. strap means connected to the inflatable body for securing the body to the hand, the strap means including a pair of straps connected at each end of the body, one of the straps of each pair located to be secured to a strap on the other pair over the first digits of the fingers and the other straps of both pairs located to be secured over each other to the hand on the side of the knuckles opposite the fingers, whereby the fingers can be maintained in an immobilized position;
    c. inflation means for selectively inflating and deflating the body.

11. The splint of claim 10, wherein the body gradually decreases in diameter from one end to the other end.

12. The splint of claim 10, wherein the straps of one pair include loop gender fasteners and the straps of the other pair include grappling gender fasteners.

13. The splint of claim 10, wherein the two pairs of straps are connected at opposite ends of the body.

14. The splint of claim 13, wherein the body includes a button at each end, the button having a stem portion, resilient clip means on the stem portion of each button with a constriction for holding the clip means in place, each pair of straps being connected to one of the clip means.

* * * * *